(12) United States Patent
Higaki

(10) Patent No.: US 6,527,982 B2
(45) Date of Patent: Mar. 4, 2003

(54) WOOD PRESERVATIVE ADDITIVE COMPOSITION

(75) Inventor: Miyato Higaki, Tokyo (JP)

(73) Assignee: Sun Technochemicals Co., Ltd., Tokyo (JP)

( * ) Notice: Subject to any disclaimer, the term of this patent is extended or adjusted under 35 U.S.C. 154(b) by 0 days.

(21) Appl. No.: 09/987,141

(22) Filed: Nov. 13, 2001

(65) Prior Publication Data

US 2002/0083864 A1 Jul. 4, 2002

(30) Foreign Application Priority Data

Nov. 13, 2000 (JP) ........................................ 2000-345079

(51) Int. Cl.⁷ .............................. C09K 3/00; C09D 5/14
(52) U.S. Cl. .................. 252/384; 106/18.32; 106/15.05
(58) Field of Search ........................... 106/18.32, 15.05; 252/384

(56) References Cited

U.S. PATENT DOCUMENTS

| | | | |
|---|---|---|---|
| 5,174,997 A | | 12/1992 | Zierke et al. |
| 5,200,421 A | * | 4/1993 | Ludwig ........................ 514/383 |
| 5,217,995 A | * | 6/1993 | Richardson ................. 514/521 |
| 5,540,954 A | * | 7/1996 | Nichols ........................ 427/397 |
| 5,804,591 A | * | 9/1998 | Valcke ........................ 514/383 |
| 5,944,880 A | * | 8/1999 | Schultz ..................... 106/18.33 |
| 6,231,651 B1 | * | 5/2001 | Schultz ..................... 106/18.32 |
| 6,344,460 B1 | * | 2/2002 | Nirchio ....................... 514/274 |
| 2002/0026883 A1 | * | 3/2002 | Walker ..................... 106/18.32 |

FOREIGN PATENT DOCUMENTS

| | | |
|---|---|---|
| DE | 39 19906 A1 | 12/1990 |
| EP | 0 050 738 A1 | 5/1982 |
| EP | 0 669 191 A1 | 8/1995 |
| JP | 56-47884 | 11/1981 |
| JP | 58-22001 | 5/1983 |
| JP | 61-16242 | 4/1986 |
| WO | WO 96/26199 | 8/1996 |

* cited by examiner

Primary Examiner—Cephia D. Toomer
(74) Attorney, Agent, or Firm—Birch, Stewart, Kolasch & Birch, LLP

(57) ABSTRACT

A wood preservative additive composition which is effective against wood rot fungi (brown rot fungi, white rot fungi, soil bacteria and soft rot fungi), does not require specific treatment as defined in Water Pollution Control Law or the like, and is environmentally friendly when treating wastes. The composition has wood preservatives (Cyproconazole or the like) which are effective against brown rot fungi and/or white rot fungi, and wood preservatives (p-cumylphenol or the like) which are effective against soil bacteria and/or soft rot fungi.

9 Claims, No Drawings

WOOD PRESERVATIVE ADDITIVE COMPOSITION

BACKGROUND OF THE INVENTION

1. Field of the Invention

The present invention relates to a wood preservative additive composition, which is ecologically friendly, easy to handle and is stable.

2. Description of the Related Art

Wood preservatives and antimold agents have a long history, and various kinds thereof are known. For example, one of the materials known from a long time ago is creosote oil, which is obtained by distillation of coal tar and is defined by JIS K2439. The creosote oil has good permeability, weather resistance and preservative property, but has problems such as odor, skin irritation, health damage, and a black color. For this reason, the purpose of the use and usage of the creosote are limited, and it is mainly used to wood contacting soil at outdoors such as electric light poles or railroad ties.

Pressure wood preservative, which is considered to have wood preservative ability most at present and is most widely used, is a fixing CCA type wood preservative (wood preservative composition with Cr compound, a Cu compound and an As compound). This is a water-soluble preservative obtained by mixing chromium compound, copper compound and arsenic compound, and its composition is defined by JISK1570. However, since this preservative contains a plurality of heavy metals regarded as questionable, it is difficult to meet the environmental problem represented by the strengthening of the regulation of Water Pollution Control Law, the problem of waste wood treated with CCA or the like. Thus, the development of a wood preservative in place of the CCA type wood preservative additive composition is desired.

Under these circumstances, many wood preservatives such as didecyldimethylammonium chloride (DDAC), copper-alkyl ammonium compounds (ACQ), metal salts of naphthenic acid (NCU) or metal salts of naphthenic acid (NZN) are proposed. The above-mentioned preservatives are wood preservatives, which do not contain a plurality of heavy metal compounds (these wood preservatives are sometimes called non-CCA type wood preservatives) differing from the CCA type wood preservatives. However, there is a serious problem in that, differing from the CCA type wood preservatives, these non-CCA type wood preservatives are effective to a part of wood rot fungi (brown wood rot fungi, white wood rot fungi, wood rot soil bacteria, wood soft rot fungi or the like), but do not almost exhibit their preservative effect to another part of the wood rot fungi.

That is, of the wood rot fungi, the non-CCA type wood preservatives have been developed for the purpose of attaining preservative property to the most general basidiomycetes (that is one kind of fungi to which brown wood rot fungi and white wood rot fungi belong, and the representative fungi are fomitopsispalustris and trametes versicolor). However, although the above-mentioned non-CCA type wood preservatives are effective to the basidiomycetes, the preservative property is not recognized to wood rot soil bacteria or wood soft rot fungi (ascomycetes inperfect fungi) that grow in an environment different from that of the basidiomycetes. For this reason, even if woods are subjected to preservative treatment using the above-mentioned non-CCA wood preservatives, in the case where such woods are used as bridge pier materials or stakes that are used being in contact with soil or in the case where such woods are used in an environment having high water content, the woods rot at a relatively early stage. Thus, treatments of, for example, repeating preservative treatment or frequently replacing the woods have been indispensable.

SUMMARY OF THE INVENTION

Non-CCA type wood preservatives are desired which are effective to all of brown wood rot fungi, white wood rot fungi, wood rot soil bacteria and wood soft rot fungi that rot wood. However, wood preservatives and wood preservative additive compositions that can answer to the requirement are not yet found at present.

Accordingly, an object of the present invention is to provide a wood preservative additive composition that is capable of meeting environmental problems such as the regulation of Water Pollution Control Law or the problem of waste wood treated with CCA by combining non-CCA type wood preservatives that are effective against wood rot soil bacteria or wood soft rot fungi but are not effective against brown wood rot fungi or white rot fungi, with non-CCA type wood preservatives that are effective to brown wood rot fungi and white wood rot fungi but are not effective to wood rot soil bacteria or wood soft rot fungi.

Therefore, the present invention is a wood preservative additive composition, characterized by comprising wood preservatives which have a microbicidal activity to brown wood rot fungi and/or white wood rot fungi, and wood preservatives which have a microbicidal activity to wood rot soil bacteria and/or wood soft rot fungi.

The preferred aspect in the wood preservative additive composition according to the present invention is characterized in that the wood preservatives which have a microbicidal activity to wood rot soil bacteria and/or wood soft rot fungi are p-cumylphenols or derivatives thereof.

The preferred aspect in the wood preservative additive composition according to the present invention is characterized in that the wood preservatives which have a microbicidal activity to brown wood rot fungi and/or white wood rot fungi are at least one selected from the group consisting of alkyl ammonium compounds, naphthenic acid and its metal salts, metal salts of versatic acid, and triazole type compounds.

The particularly preferred aspect in the wood preservative additive composition according to the present invention is characterized in that the wood preservatives which have a microbicidal activity to wood rot soil bacteria and/or wood soft rot fungi are p-cumylphenols.

Also, the particular preferred aspect in the wood preservative additive composition according to the present invention is characterized in that the wood preservatives which have a microbicidal activity to brown wood rot fungi and/or white wood rot are didecyldimethylammonium chloride (DDAC), BARDAP, copper naphthenate, Cyproconazole [(2RS,3RS;2RS,3SR)-2-(4-chlorophenyl)-3-(cyclopropyl-1-(1H-1,2,4-triazol-1-yl)butan-2-011], Tebuconazole [(RS)-1-p-chlorophenyl-4,4-dimethyl-3-(1H-1,2,4-triazol-1-ylmethyl)pentan-3-ol], or Propiconazole [1-[2-(2,4-dichlorophenyl)-4-propyl-1,3-dioxoran-2-ylmethyl]-1H-1,2,4-triazole].

DETAILED DESCRIPTION OF THE INVENTION

The wood preservative additive composition of the present invention is effective to the above-mentioned wood rot fungi, and also effective to disinfection of so-called mold (part of ascomycetes, mastigomycotina, zygomycetes) and antitermite. Therefore, the composition of the present invention should correctly be called a wood preservative, antimold agent and antitermite additive composition, but is called a wood preservative additive composition for convenience sake (it may be called a "preservative" for simplicity).

A first component which constitutes the wood preservative additive composition of the present invention is a compound which is effective to growth inhibition and prevention (disinfection) of mainly basidiomycetes (fomitopsispalustris or the like), ascomycetes (trametes versicolor or the like) and inperfect fungi, which are brown wood rot fungi or white wood rot fungi. The preservative does not substantially show the effect to disinfection of wood rot soil bacteria or wood soft rot fungi.

The wood preservatives which have a microbicidal activity to brown wood rot fungi and/or white wood rot fungi are alkylammonium compounds, naphthenic acid and its metal salts, metal salts of versatic acid, triazole type compounds and organic iodine type compounds. One kind or a mixture of two kinds or more selected from those is used.

The triazole type compounds are preferably in that such can exhibit the appropriate effect even if the treatment amount (application amount) to woods is about 150–800 g/m$^3$ which is almost the half, as compared with the conventional wood preservative CCA.

Specifically, examples of the wood preservative include alkylammonium compounds such as didecyldimethylammonium chloride (DDAC), BARDAP (N,N-didecyl-N-methylpolyoxyethylammonium propionate), copper benzaIconium chloride (ACQ) or N-alkylbenzyldimethylammonium chloride (BKC); metal salts of naphthetic acid such as copper naphthenate or zinc naphthenate; metal salts of versatic acid such as zinc versatate; triazole type compounds such as Cyproconazole [(2RS,3RS;2RS,3SR)-2-(4-chlorophenyl)-3-(cyclopropyl-l-(lH-1,2,4-triazol-1-yl)butan-2-01], Tebuconazole [(RS)-l-p-chlorophenyl-4,4-dimethyl-3-(1H-1,2,4-triazol-l-ylmethyl) pentan-3-0l], Propiconazole [1-[2-(2,4-dichlorophenyl)-4-propyl-1,3-dioxoran-2-ylmethyl]-lH-1,2,4-triazole], 1-[2-(2', 4-dichlorophenyl-1,3-dioxoran-2-ylmethyl]-1H-1,2,4-triazol-l-ethanol or 1-[2-(2',4'-dichlorophenyl)-4-propyl-l,3-dioxoran-2-ylmethy1]-lH-1,2,4-triazol-1-ethanol; and organic iodine compounds such as IF-1000[4-chlorophenyl-3-iodopropargyl formal] or IPBC [3-iodo-2-propynyl-N-butylcarbamate].

The above-mentioned wood preservatives can be used in combination. Preferable combination is Cyproconazole and DDAC; Cyproconazole and BARDAP; Tebuconazole and Propiconazole; and the like.

A second component which constitutes the wood preservative additive composition of the present invention is a compound which is effective to growth inhibition and prevention (disinfection) of wood rot soil bacteria and wood soft rot fungi, mainly wood soft rot fungi mainly such as chaetomium globosum. The preservative does not substantially show the effect in a practical level to disinfection of brown wood rot fungi or white wood rot fungi.

Specifically, examples of the wood preservatives include p-cumylphenol (PCP), and its salts such as sodium salt of p-cumylphenol or ethylamine salt of p-cumylphenol. PCP exhibits the effect to growth inhibition or disinfection of wood rot soil bacteria in addition to ascomycetes and inperfect fungi. Further, PCP is effective as antimold agent and antitermite. Therefore, PCP is particularly preferable.

PCP can exhibit a sufficient effect to woods in the treatment amount (application amount) of about 200–1,000 g/m$^3$.

Dinitrophenol, dinitro-o-cresol, chloronitrophenol and the like known as phenol type microbicides of woods do not have an microbicidal activity to ascomycetes, and are therefore not included in the wood preservatives of the present invention.

The wood preservative additive composition of the present invention can contain general additives for wood preservatives. For example, petroleum resins, rosins and waxes can reinforce microbicidal activity of PCP and impart sustainability, and therefore are preferable additives.

Antitermite agents and insecticide may be mixed with the wood preservative additive composition of the present invention so long as it does not depart from the object of the present invention. Examples of the antitermite agents include Permetorin, Imidachlopride, Etpfenplox.

The wood preservative additive composition of the present invention is advantageously, on handleability, used in the form of an emulsion or dispersion by emulsifying or dispersing the first component and the second component in water. The composition can also be used in the form of a solution of the first and second components dissolved in an organic solvent or in the form of granules obtained by supporting the first and second components on carriers.

Those forms can be prepared by the conventional method. For example, each preservative component and additives are simultaneously or successively added to water in the presence of an emulsifier or a dispersant, followed by mixing under stirring. The content of the first component in the emulsion or dispersion is 0.05 to 10 kg/m$^3$, preferably 0.1 to 5 kg/m$^3$, and the content of the second component therein is 0.1 to 5 kg/m$^3$, preferably 0.3 to 2 kg/m$^3$.

Examples of the emulsifier include nonionic surfactants such as polyoxyethylene alkylphenol ether, polyoxyethylene styrenated phenol ehter or polyoxyethylene castor oil ether; and anionic surfactants such as polyoxyethylene alkylphenol ether sulfates or polyoxtethylene alkyl ether sulfates. Of those, polyoxyethylene alkylphenol ether sulfates are preferably used.

Examples of the dispersant include the above-mentioned nonionic surfactants, and polyoxyethylene castor oil ether is preferably used.

The solvent used in forming a solution is not particularly limited, and hydrocarbons (benzene, toluene or the like), alcohols (methanol, ethanol, propylene glycol, polyethylene glycol or the like), esters (ethyl acetate or the like), ketones (acetone or the like), ethers, dimethylsulfoxide and the like are used. Concentration and mixing ratio of the first component and second component in the solution can substantially the same degree as in the emulsion or dispersion.

The carrier used in preparing granules is not particularly limited, and silica, talc, bentonite and the like are used.

The wood preservative additive composition of the present invention is particularly excellent in applying to woods. In applying to woods, methods such as coating, spraying, immersion, diffusion, pressure injection or the like can be used. Of those, pressure injection is preferably used from the standpoints of efficiency of preservative treatment step, breadth of permeation range of the preservative additive composition, dispersibility of the preservative additive composition and the like. In the case where the form of wood is a veneer or plywood, there may be the case that coating, spraying or immersion are preferable.

The treatment amount (application amount) to woods, for example, in case of using triazole compound and PCP in combination, about 150 to 800 g/m$^3$ of triazole type compound and about 200 to 1,000 g/m$^3$ PCP are sufficient.

Of course, the wood preservative additive composition of the present invention is also useful as preservatives and antimold agents of inedible substances such as leathers, papers, fibers, pastes, adhesives, paints, lubricants or the like. Methods of applying to the inedible substances the wood preservative additive composition of the present invention can be conducted by the conventional methods.

The pressure injection method is a method of permeating a wood preservative additive composition in woods by combining pressurizing and reduced pressure using a pump. The method consists of, for example, pre-exhausting at about 660 mmHg, pressuring to a range of from 392 to 2,157 kPa or higher to permeate, and post-exhausting at −66 kPa or lower. The entire amount of the preservative introduced into a closed space is not always injected in woods.

Prior to the preservative treatment, the wood is preferably dried to control to an appropriate water content, or subjected to pretreatment for facilitating permeation of the preservative. Conventional known methods can appropriately be used as the pretreatment.

Cut surface exposed as a result of cutting the preservative-treated wood is preferably subjected to post-treatment such as the preservative treatment by the wood preservative additive composition of the present invention or the like, separately. Conventional known methods can appropriately be used as the post-treatment.

EXAMPLES 1 to 8 AND COMPARATIVE EXAMPLES 1 to 6

Wood preservatives shown in Tables 1 and 2 (brown and white rot fungi; soil bacteria and soft rot fungi) in the proportion shown in Tables 1 and 2 were mixed under stirring with additives shown in Tables 1 and 2 (petroleum resin: ARKON, manufactured by Arakawa Kagaku Kogyo K.K.; emulsifier: polyoxyethylene alkyl ether sulfate; dispersant: polyoxyethylene castor oil ether; solvent: aromatic solvent) to prepare wood preservative additive compositions in emulsion state or dispersion state. Those compositions were subjected to the following evaluation tests.

Preservative Performance Test I:

Preservative performance test of wood preservative additive compositions to brown and white rot fungi was conducted according to the provision of JIS K1571 (performance standard of wood preservative and test method) using a cedar wood (water content: 15% by mass) to measure mass loss of the cedar wood. When the loss was 3% or less, it was designated "pass". The results obtained are shown in Tables 1 and 2.

Preservative Performance Test II:

Preservative performance test of wood preservative additive compositions to soil microbes, particularly soft rot fungi, was conducted with an improved funguscellar method described below. Forest soil A layer was introduced into a 900 ml volume mayonnaise bottle up to the half of the volume, and water content was adjusted to 80–90 in terms of WHC (Water Holding Content). Test specimens treated according to JIS K1571 were embedded in the soil in the proportion of 3 test specimens/bottle. The bottle was placed in a thermostat at a temperature of 26±2° C. and a humidity of 90%, and maintained therein for one year. The bottle was taken out of the thermostat after one year, and mass loss of the test specimens was measured. When the loss was 3% or less, it was designated "pass". Non-treated test specimen has the mass loss of 10% or more. The results obtained are shown in Tables 1 and 2.

The wood preservative additive composition of the present invention does not have a fear of affecting skin, mucosa or the like, health injury or environmental injury, as compared with wood preservatives containing a plurality of heavy metals, such as CCA wood preservatives, and also is effective to growth inhibition and prevention (disinfection) of brown wood rot fungi, white wood rot fungi, wood rot soil bacteria and wood soft rot fungi, which are wood rot fungi, has excellent sustainability, and does not generate uncomfortable odor and coloration. Therefore, the wood preservative additive composition can be used in various fields and for applications such as buildings, civil engineering, furniture and the like.

TABLE 1

|  | Example 1 | Example 2 | Example 3 | Example 4 | Example 5 | Example 6 | Example 7 | Example 8 |
|---|---|---|---|---|---|---|---|---|
| Preservative Components* | | | | | | | | |
| Brown and white rot fungi | | | | | | | | |
| DDAC | 4.5 | 0 | 0 | 0 | 0 | 0 | 0 | 0 |
| BARDAP | 0 | 4.5 | 0 | 0 | 0 | 0 | 0 | 0 |
| ACQ | 0 | 0 | 2.6 | 0 | 0 | 0 | 0 | 0 |
| Copper naphthenate | 0 | 0 | 0 | 1.0 | 0 | 0 | 0 | 0 |
| zinc naphthenate | 0 | 0 | 0 | 0 | 1.6 | 0 | 0 | 0 |
| Cyproconazole | 0 | 0 | 0 | 0 | 0 | 0.13 | 0 | 0 |
| Teburonazole | 0 | 0 | 0 | 0 | 0 | 0 | 0.18 | 0 |
| Propiconazole | 0 | 0 | 0 | 0 | 0 | 0 | 0.18 | 0 |
| IF-1000 | 0 | 0 | 0 | 0 | 0 | 0 | 0 | 1.0 |
| Soil bacteria and soft rot fungi | | | | | | | | |
| PCP | 1 | 1 | 1 | 1 | 0 | 1 | 1 | 1 |
| PCP-Na | 0 | 0 | 0 | 0 | 1 | 0 | 0 | 0 |
| Additives | | | | | | | | |
| Petroleum resin | added | none | none | none | none | added | none | none |
| Emulsifier/ dispersant | added | added | added | added | added | added | added | added |

TABLE 1-continued

|  | Example 1 | Example 2 | Example 3 | Example 4 | Example 5 | Example 6 | Example 7 | Example 8 |
|---|---|---|---|---|---|---|---|---|
| Aromatic solvent | added | added | added | added | added | added | added | added |
| Water | added | added | added | added | added | added | added | added |
| Results of Preservative Performance Test** | | | | | | | | |
| JIS K1571 | | | | | | | | |
| Fomitopsispalustris | 2.4 ± 0.1 | 2.9 ± 0.09 | 2.6 ± 0.2 | 1.8 ± 1.09 | 2.7 ± 0.21 | 2.6 ± 0.1 | 2.1 ± 0.3 | 1.4 ± 1.01 |
| Trametes versicolor | 1.3 ± 0.4 | 0.7 ± 0.1 | 1.2 ± 0.2 | 0.9 ± 0.0 | 1.1 ± 0.9 | 1.6 ± 0.6 | 0.8 ± 0.0 | −1.2 ± 0.0 |
| Improved funguscellar method | | | | | | | | |
| Chaetomium globosum | −1.8 ± 0.0 | 0.9 ± 0.0 | 1.2 ± 0.0 | 0.0 ± 0.0 | 1.0 ± 0.04 | 0.7 ± 0.02 | 1.8 ± 0.3 | −0.9 ± 0.0 |

*Concentration of Preservative Components: kg/m$^3$
**Mass Loss of Wood: %

TABLE 2

|  | Comparative Example 1 | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|---|
| Preservative components* | | | | | | | | | |
| brown and white rot fungi | | | | | | | | | |
| DDAC | 0 | 0 | 0 | 0 | 0 | 0 | 4.5 | 0 | 0 |
| BARDAP | 0 | 0 | 0 | 0 | 0 | 0 | 0 | 4.5 | 0 |
| ACQ | 0 | 0 | 0 | 0 | 0 | 0 | 0 | 0 | 2.6 |
| copper naphthenate | 0 | 0 | 0 | 0 | 0 | 0 | 0 | 0 | 0 |
| zinc naphthenate | 0 | 0 | 0 | 0 | 0 | 0 | 0 | 0 | 0 |
| Cyproconazole | 0 | 0 | 0 | 0 | 0 | 0 | 0 | 0 | 0 |
| Teburonazole | 0 | 0 | 0 | 0 | 0 | 0 | 0 | 0 | 0 |
| Propiconazole | 0 | 0 | 0 | 0 | 0 | 0 | 0 | 0 | 0 |
| IF-1000 | 0 | 0 | 0 | 0 | 0 | 0 | 0 | 0 | 0 |
| soil bacteria and soft rot fungi | | | | | | | | | |
| PCP | 3 | 5 | 10 | 0 | 0.5 | 1 | 0 | 0 | 0 |
| PCP-Na | 0 | 0 | 0 | 5 | 0 | 0 | 0 | 0 | 0 |
| additives | | | | | | | | | |
| petroleum resin | none | none | none | none | none | none | added | none | none |
| emulsifier/dispersant | added | added | added | added | added | added | added | added | added |
| aromatic solvent | added | added | none | added | none | none | added | added | added |
| water | none | none | none | added | none | none | added | added | added |
| Results of Preservative Performance Test** | | | | | | | | | |
| JIS K1571 | | | | | | | | | |
| Fomitopsispalustris | 42.1 ± 13.1 | 43.6 ± 11.8 | 12.6 ± 6.4 | 44.1 ± 13.1 | 60.7 ± 1.0 | 61.7 ± 1.0 | 1.2 ± 0.8 | 2.9 ± 0.3 | 1.1 ± 0.6 |
| trametes versicolor | 11.8 ± 4.6 | 8.4 ± 2.8 | 13.9 ± 2.8 | 12.6 ± 6.4 | 28.3 ± 2.6 | 24.0 ± 6.0 | 1.4 ± 0.2 | 1.8 ± 0.9 | 0.7 ± 0.1 |
| improved funguscellar method | | | | | | | | | |
| chaetonium globosum | 1.2 ± 0.0 | 0.9 ± 0.1 | 0.0 ± 0.0 | −1.2 ± 0.0 | 1.3 ± 0.0 | 1.0 ± 0.3 | 13.3 ± 2.2 | 12.6 ± 1.5 | 14.5 ± 0.9 |

*Concentration of Preservative Components: kg/m$^3$
**Mass Loss of Wood: %

What is claimed is:

1. A wood preservative additive composition comprising: wood preservatives having a microbicidal activity to brown wood rot fungi and/or white wood rot fungi; and wood preservatives having a microbicidal activity to wood rot soil bacteria and/or wood soft rot fungi; wherein the wood preservative having a microbicidal activity to wood rot soil bacteria and/or wood soft rot fungi is a p-cumylphenol or a salt thereof.

2. The wood preservative additive composition according to claim 1, wherein the wood preservative having a microbicidal activity to brown wood rot fungi and/or white wood rot fungi is at least one selected from the group consisting of alkyl ammonium compounds, naphthenic acid and its metal salts, metal salts of versatic acid, and triazole compounds.

3. The wood preservative additive composition according to claim 1, wherein the wood preservative having a microbicidal activity to brown wood rot fungi and/or white wood rot fungi is at least one selected from the group consisting of didecyldimethylammonium, N,N-didecyl-N-methylpolyoxyethylammonium propionate, copper naphthenate, (2RS,3RS;2RS,3SR)-2-(4-chlorophenyl)-3-(cyclopropyl-1-(1H-1,2,4-triazol-1-yl)butan-2-ol, (R,S)-1- p-chlorophenyl-4,4-dimethyl-3-(1H-1,2,4-triazol-1-ylmethyl)pentan-3-ol and 1-[2-(2,4-dichlorophenyl)-4-propyl-1,3-dioxoran-2-ylmethyl]-1H-1,2,4-triazole.

4. The wood preservative additive composition of claim 1, wherein said wood preservative having microbial activity against brown wood rot fungi and/or white wood rot fungi is (2RS,3RS;2RS,3SR)-2-(4-chlorophenyl)-3-(cyclopropyl-1-(1H-1,2,4-triazol-1-yl)butan-2-ol and didecyldimethylammonium chloride.

5. The wood preservative additive composition of claim 1, wherein said wood preservative having microbial activity against brown wood rot fungi and/or white wood rot fungi is (2RS,3RS;2RS,3SR)-2-(4-chlorophenyl)-3-(cyclopropyl-1-(1H1,2,4-triazol-1-yl)butan-2-ol and N,N-didecyl-N-methylpolyoxyethylammonium propionate.

6. The wood preservative additive composition of claim 1, wherein said wood preservative having microbial activity against brown wood rot fungi and/or white wood rot fungi is (R,S)-1-p-chlorophenyl-4,4-dimethyl-3-(1H-1,2,4-triazol-1-ylmethyl)pentan-3-ol and 1-[2-(2,4-dichlorophenyl)-4-propyl-1,3-dioxoran-2-ylmethyl]-1H-1,2,4-triazole.

7. The wood preservative additive composition of claim 1, further comprising an antitermite agent.

8. The wood preservative additive composition of claim 7, wherein said antitermite agent is Permetorin, Imidachlopride or Etpfenplox.

9. The wood preservative additive composition of claim 1, wherein said wood preservative additive composition contains 200–1,000 g/m$^3$ of said p-cumylphenol or its salt thereof.

* * * * *